Figure 1:
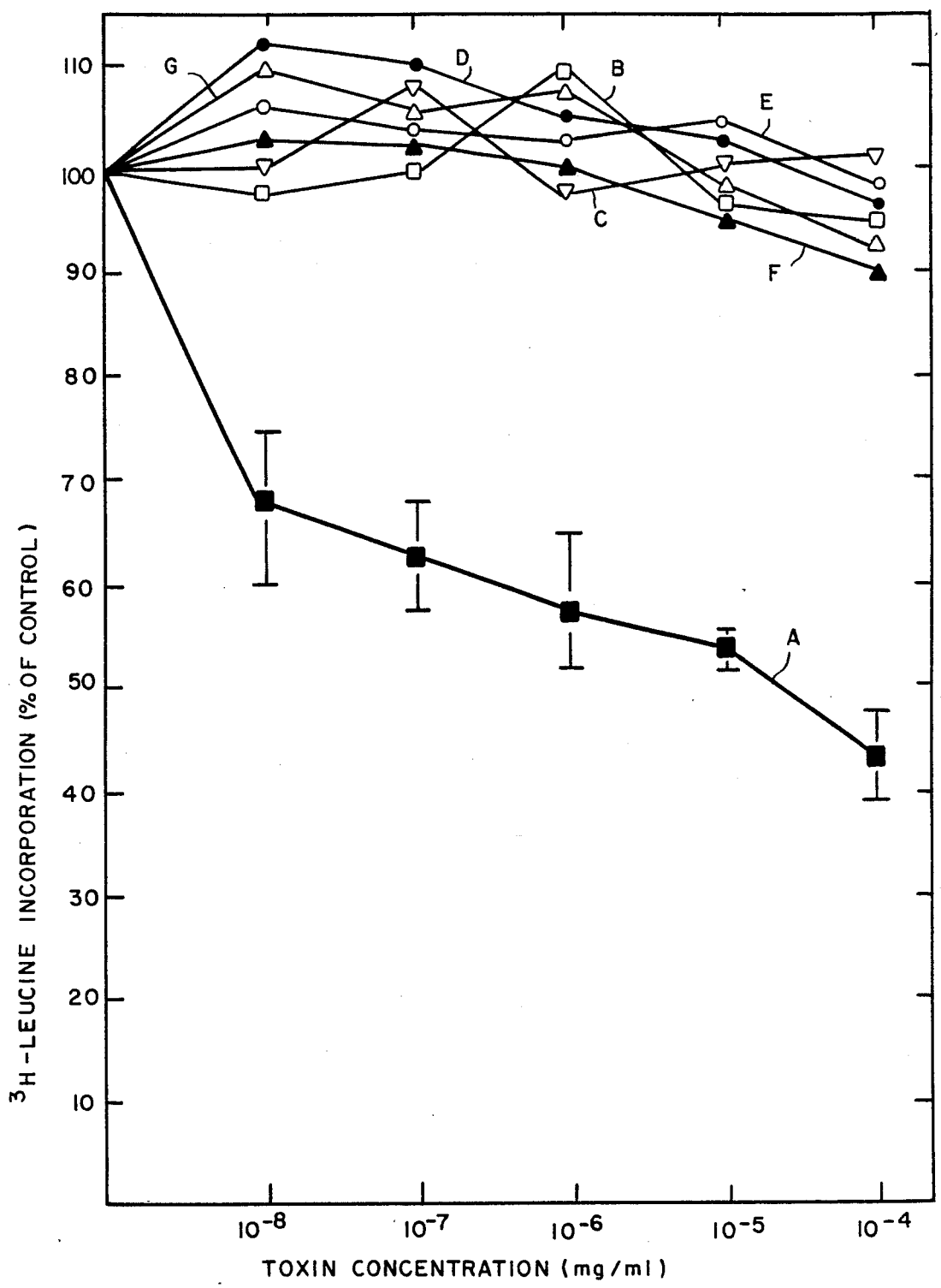

United States Patent [19]

Huang

[11] Patent Number: 4,925,661
[45] Date of Patent: May 15, 1990

[54] TARGET-SPECIFIC CYTOTOXIC LIPOSOMES

[76] Inventor: Leaf Huang, 352 Dominion Cr., Knoxville, Tenn. 37922

[21] Appl. No.: 12,240

[22] Filed: Feb. 9, 1987

Related U.S. Application Data

[63] Continuation-in-part of Ser. No. 602,177.

[51] Int. Cl.$^5$ ............... A61K 39/00; C12Q 1/02
[52] U.S. Cl. ................... 424/85.91; 424/85.8;
424/417; 424/420; 424/450; 435/29; 264/4.1;
264/4.3; 264/4.6; 530/387
[58] Field of Search ............... 424/417, 420, 450, 85,
424/85.8, 85.91; 428/422.2; 264/4.1, 4.3, 4.6,
7.1; 435/240.2, 240.1, 243, 252.1, 254, 29;
530/386, 387, 388, 389, 390, 391

[56] References Cited

U.S. PATENT DOCUMENTS 4,789,633 12/1988 Huang et al. ............... 435/240.2

OTHER PUBLICATIONS

Straubinger et al., *J. Cell Biol.*, vol. 97, 109(9), Abst. No. 420, 1983.
Huang et al., *Biochim Biophys Acta*, vol. 716, 1982, pp. 140–150, "Characterization of Antibody Covalently Coupled to Liposomes".
Jansons, *Chem. Abst.*, vol. 101(18), Abst. 1574939, "Preparation and Analysis of Antibody-Tangible Liposomes".

*Primary Examiner*—Robin L. Teskin
*Attorney, Agent, or Firm*—Ernest V. Linek; George W. Neuner

[57] ABSTRACT

The A fragment of the diphtheria toxin (DTA) was encapsulated in pH-sensitive liposomes. This novel reagent is extremely cytotoxic to cells expressing surface antigen which is recognized by the immunoliposome. The reagent is not toxic to cells which do not express the antigen. Thus, this reagent, or others similarly prepared represent potential anticancer reagents.

14 Claims, 2 Drawing Sheets

TARGET-SPECIFIC CYTOTOXIC LIPOSOMES

CROSS REFERENCE TO RELATED APPLICATIONS

This application is a continuation-in-part of copending application Ser. No. 602,177, filed 19 Apr. 1984, now allowed U.S. Pat. No. 4,789,633 the disclosure of which, to the extent necessary, is hereby incorporated herein by reference.

BACKGROUND OF THE INVENTION

Liposomes composed of phosphatidylethanolamine and oleic acid (PE/OA) become unstable and fusion-active at the weakly acidic pH of from about 5 to about 6.5. These pH-sensitive liposomes can be coated with fatty acid-derivatized antibody to enhance the cytoplasmic delivery of encapsulated molecules to antigen expressing cells.

Cytoplasmic delivery is thought to be achieved through receptor-mediated endocytosis of the immunoliposomes. The liposomes then encounter the acidic pH of the endosome and are thought to fuse with the endosome membrane, thus releasing the encapsulated contents into the cytoplasm.

SUMMARY OF THE INVENTION

The A fragment of the diphtheria toxin (DTA) has been encapsulated into pH-sensitive liposomes. This novel reagent is extremely cytotoxic to cells expressing surface antigen which is recognized by the immunoliposome. The reagent is not toxic to cells which do not express the antigen. Thus, this reagent, or others similarly prepared, represent potential anticancer reagents.

The present invention is also directed to the use of the fragment A of diphtheria toxin (DTA) as a marker for cytoplasmic delivery.

The pH-sensitive immunoliposomes of the present invention are able to overcome the translocation block in DT-resistant L929 cells. It is believed that these liposomes are able to release DTA from an acidic cellular compartment by fusion with the endosome membrane.

BRIEF DESCRIPTION OF THE DRAWINGS

FIG. 1 illustrates the inhibition of protein synthesis by free or liposome encapsulated toxins. Group (A) represents PE/OA immunoliposomes containing DTA; Group (B) represents PE/OA liposomes containing DTA; Group (C) empty PE/OA immunoliposomes; Group (D) PC Immunoliposomes containing DTA; Group (E) PC liposomes containing DTA; Group (F) DT alone; and Group (G) represents DTA alone.

FIG. 2 illustrates the blocking of cytotoxicity mediated by DTA encapsulated in pH-sensitive immunoliposomes. The data presented are; I-PE/OA (DTA): pH-sensitive immunoliposomes containing DTA; and E/OA (empty): pH-sensitive immunoliposomes not containing DTA.

DETAILED DESCRIPTION OF THE PREFERRED EMBODIMENTS

It is known that diphtheria toxin (DT) resistant mouse cells bind and internalize DT normally (Keen, J. H., et al., *Proc. Natl. Acad. Sci. USA,* 79: 2912–2916 (1982) and L929 cells possess a DT-sensitive elongation factor 2, see for example, Guillemot, J. C., et al., *Cell Phys.,* 122: 193–199 (1985); Nakanishi, M., et al., *Exp. Cell. Res.,* 159: 399–409 (1985); Uchida, T., et al., *Cell Biol.,* 80: 10–20 (1979) and Yamazumi, M., et al., *Cell.* 15: 245–250 (1978)). Thus, DT resistance in L929 cells seems to result from a block in the translocation of fragment A from the endosome into the cytoplasm.

DTA irreversibly inhibits protein synthesis in eukaryotes by enzymatically inactivating elongation factor 2, (Pappenheimer, A. M., Jr., *Ann. Rev. Biochem.,* 46: 69–94 (1977)). DTA is non-toxic to either animals or cultured cells because it cannot reach the cytoplasm (Keen et al., supra: Pappenheimer, supra; Gill, D. M., et al., *J. Biol. Chem.,* 246: 1492–1495 (1971) and Gill, D. M., et al., *J. Biol. Chem.,* 246: 1485–1491 (1971)).

It has been shown, however, that DTA is toxic if introduced into the cell by artificial means (Guillemot et al., supra: Nakanishi et al., supra; Uchida et al., supra: Yamazumi et al., supra).

In accordance with the findings of other investigators, incubation of L929 cells with unencapsulated DTA or DT had no effect on protein synthesis as measured by [3H]-leucine incorporated into newly synthesized proteins. (FIG. 1).

We encapsulated DTA in liposomes prepared by a modification of the dehydration-rehydration method, Kirby, C., et al., *Biotechnology,* 1: 979–984 (1984). This method was chosen since it does not require exposure of encapsulated contents of either sonication or organic solvents as do other methods of liposome preparation. Furthermore, incorporation of palmitoyl antibody (Huang, L., et al., in *Liposome Technology,* Vol. 3 79–108. CRC Press, Boca Raton, Fla. (1983)) could be readily achieved by including the antibody in the rehydration mixture. We have used a mouse monoclonal antibody to the major histocompatability antigen H-2K (k) to prepare the immunoliposomes since DTA resistant mouse L929 cells express this surface antigen. (Connor and Huang, supra: and Huang et al., supra).

We prepared DTA-containing pH-sensitive immunoliposomes composed of phosphatidylethanolamine (PE)/oleic acid (OA) (8:2 molar ratio) (Connor, Yatkin and Huang, supra) and pH-insensitive immunoliposomes composed of phosphatidylcholine (PC) using this method. We also prepared DTA-containing liposomes without antibody and empty pH-sensitive immunoliposomes of the same lipid composition.

The toxicity of the liposome preparations to L929 cells is shown in FIG. 1. pH-insensitive PC liposomes containing DTA did not inhibit protein synthesis in the concentration range used. Toxicity of PC liposomes could not be enhanced by incorporation of antibody into the liposome membrane.

It has been shown previously that PC liposomes do not release their encapsulated contents into the cytoplasm, since they are delivered to the lysosomes and degraded. (see, Connor and Huang, supra). DTA-containing pH-sensitive liposomes without antibody were also non-toxic. This is probably due to a lack of sufficient binding and internalization of the liposomes. When DTA-containing pH sensitive immunoliposomes were incubated with the cells, a dose-dependent inhibition of protein synthesis was observed. This indicates the release of active DTA into the cytoplasm. Empty pH-sensitive immunoliposomes had no effect on protein synthesis.

To see if endosome/lysosome acidification was required for pH-sensitive immunoliposome-mediation release of DTA, we did the cytotoxicity experiments in the presence of NH₄Cl and chloriquine. These drugs are weak bases which raise the pH of the endosome/lysosome interior (Ohkuma, S., et al., *Proc. Natl. Acad. Sci. USA*, 75: 3327–3331 (1978) and Helenius, A., et al., *J. Gen. Virol.*, 58: 47–61 (1982).

Figure 2:
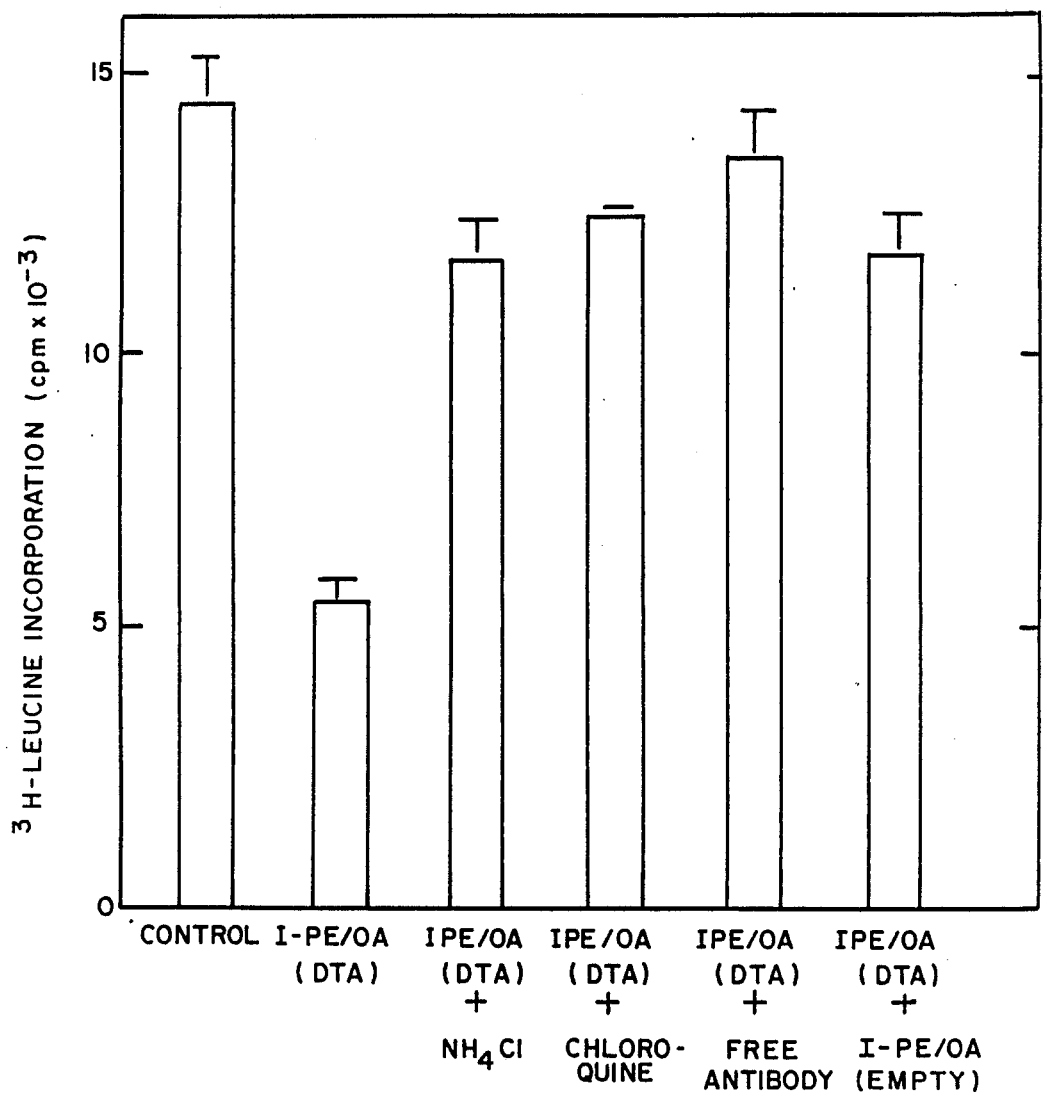

Cells which were preincubated with either NH₄Cl or chloriquine prior to immunoliposome addition were (Huang et al., *Biochem. Biophys. Acta*, 716: 140–150 (1982)) protected from intoxification by immunoliposome-encapsulated DTA (FIG. 2). Neither NH₄Cl nor chloroquine alone had an effect on protein synthesis (Huang et al., supra). Therefore endosome/lysosome acidification appears to be required for pH-sensitive immunoliposome-mediated translocation of DTA into the cytoplasm.

We also investigated the dependence of our delivery system on specific cell-surface binding immunoliposomes. Cells were pre-incubated for one hour in the presence of an excess of free antibody prior to immunoliposome addition. As seen in FIG. 2, such cells were protected from the toxic effect of DTA. Pre-treatment of cells with empty pH-sensitive immunoliposomes before addition of DTA-containing immunoliposomes also effectively blocked DTA delivery.

It has been shown that DT-resistant mouse cells are not defective in the binding and internalization of DT (Keen et al., supra) rather, there is a block in the translocation of DTA from the endosome into the cytoplasm. The observation that the pH-sensitive immunoliposomes are able to bypass the translocation block suggests that the site of DTA release from the liposomes is at the endosome.

This notion is supported by the observation that NH₄Cl and chloroquine inhibited the observed cytotoxicity. These drugs (Huang et al., supra) are known to inhibit a variety of cellular events which require the acidification of the endosome, such as the release of the Semliki Forest Virus genome (Helenius, et al., supra and the translocation of DTA in the DT-sensitive cells. (Sandvig, K., et al., *J. Cell. Biol.*, 87: 828–832 (1980)).

It is also consistent with preliminary results in which pH-sensitive immunoliposomes were able to mediate the cytoplasmic delivery of cytosine arabinoside. Cytosine arabinoside is a cytotoxic drug which is lysosome-sensitive in that exposure of the drug to lysosomal enzymes leads to its degradation and inactivation, (Rustum, Y. M., et al., *J. Eur. J. Clin. Oncol.*, 17: 809–817 (1981).

It is therefore suggested that the pH-sensitive immunoliposomes release their contents into the cytoplasm from the endosomes and the release step depends on the acidification of the organelle. The release of the liposome contents is probably the result of liposome-endosome fusion, because it has been shown that pH-sensitive liposomes become fusion-competent at pH 5–6.5 (Duzgunes, N., et al., *Biochem.*, 24: 3091–3098 (1985) and Huang et al., supra) which is the range of the endosome pH (Maxfield, F. R., *J. Cell Biol.*, 95: 676–681 (1982)).

Another possible mechanism of release is that pH-sensitive immunoliposomes become leaky and release DTA into the endosome interior. DTA then translocates itself into the cytoplasm as free toxin. This is not likely since it has been shown that DTA alone cannot cross lipid membranes in the absence of the B fragment of DT, (Donovan, J. J., et al., *J. Biol. Chem.*, 260: 8817–8823 (1985)).

Another alternative is that pH-sensitive immunoliposomes induce endosome rupture, thereby releasing DTA into the cytoplasm. While the last mechanism cannot be distinguished from liposome-endosome fusion at the present time, the system introduced in this work is more effective for cytoplasmic delivery of DTA than either DTA-antibody or DTA-hormone conjugates, (Esworthy, R. S., et al., *J. Biol. Chem.*, 259: 11496–11504 (1984) and Cawley, D. B., et al., *Cell.* 22: 563–570 (1980)).

Presumably, the lack of toxicity of these conjugates results from ineffective translocation of DTA into the cytosol since significant toxicity was obtained only in the presence of added diphtheria B fragment. (Esworthy and Neville, supra). In contrast, our system delivers DTA effectively in the absence of B fragment.

It is clear that pH-sensitive immunoliposomes may be useful for the targeted, cytoplasmic delivery of other biologically active macromolecules such as antibodies, enzymes and DNA.

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

EXAMPLE 1

Liposomes were prepared by drying appropriate lipids under $N_2$ gas followed by vacuum desiccation. The lipid film was resuspended in phosphate-buffered saline (PBS) and sonicated to form small unilamellar vesicles (SUV). For PE/OA liposomes and immunoliposomes pH was adjusted to 8.0–8.5 by using 0.1N NaOH.

EXAMPLE 2

A 0.2 mg/ml solution of DTA in PBS was added to the SUV of Example 1 and the mixture was frozen and lyophilized The freeze-dried preparation was rehydrated with 1/10 of the original SUV volume of either palmitic acid-derivatized antibody (Huang, et al., supra) in 0.15% deoxycholate, PBS, pH 8.0 (for immunoliposomes) or PBS pH 8.0 (for liposomes).

The volume was brought up to 1 ml with PBS and the mixture was extruded through a 0.2 micron filter (Nucleopore). Unencapsulated DTA was separated from liposomes by passage over a Sephadex G-200 column (Pharmacia). The average trapping efficiency for the liposome preparations used was 10% of the available DTA. Antibody incorporated into liposome membranes ranged from 38–50% in different experiments. The immunoliposomes used in this study contained 0.8 micromoles DTA and 4 micro-moles palmitoyl antibody per 16.5 micro-moles of total lipid.

EXAMPLE 3

Mouse L929 cells (k haplotype) were seeded (10-3 cells/well) into 96 well disposable plates (Corning) the day before the experiment. The medium (McCoy's 5A, supplemented with 10% fetal calf serum) was then removed and fresh medium containing immunoliposomes, liposomes or free toxin was added.

After 3 hours at 37° C. the medium was removed and the cells were washed and fresh medium was added. After 18 hours the medium was replaced with leucine-free McCoy's medium. 2 micro-Ci per well of [$^3$H]-leucine was added and incubation was continued for an additional 6 hr. The cells were harvested and processed for scintillation counting as described by Esworthy et al., supra.

Results are expressed as the percentage of the incorporation of [$^3$H]-leucine into TCA insoluble material in the untreated controls. Control cells incorporated between 4,000 to 18,000 cpm in different experiments. All experiments were done in quadruplicate. Error bars were included only for immunoliposomes containing DTA for the sake of clarity. The magnitude of error for the other treatments did not differ significantly from that shown for DTA-containing immunoliposomes.

One hour prior to immunoliposome addition 50 micro-M NH$_4$Cl, 50 micro-M chloroquine, free anti-H-2Kk antibody (10-fold excess) or empty immunoliposomes (5-fold excess) were added. Cells were incubated with DTA-containing immunoliposomes, washed, labeled with $^3$HI-leucine and treated as described above.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. Target specific immunoliposomes consisting essentially of antibody coated, pH-sensitive liposomes of 8:2 molar ratio of phosphatidylethanolamine and oleic acid, said liposomes containing at least one entrapped cytotoxic reagent.

2. The target specific immunoliposomes of claim 1, wherein the entrapped cytotoxic reagent is fragment A of the diphtheria toxin.

3. The target specific immunoliposomes of claim 1, wherein the antibody coating includes a long chain ($C_{12}$–$C_{24}$) fatty acid segment.

4. The target specific immunoliposomes of claim 3, wherein the fatty acid segment is derived from palmitic acid.

5. The target specific immunoliposomes of claim 1, wherein the antibody is a monoclonal antibody.

6. The target specific immunoliposomes of claim 1, wherein the antibody a specific antigen on the surface of target cells.

7. The target specific immunoliposomes of claim 6, wherein the specific antigen recognized by the antibody is the major histocompatability antigen H-2K.

8. A method of delivering cytotoxic reagents to cells comprising the steps of:
    (a) preparing pH-sensitive immunoliposomes from phosphatidylethanolamine and oleic acid in a molar ratio of (8:2) and a fatty acid derivatized antibody;
    (b) entrapping an effective amount of a cytotoxic reagent in the pH-sensitive immunoliposome; and
    (c) administering said immunoliposomes containing the cytotoxic reagent to cells expressing an antigen which is recognized by said antibody.

9. The method of claim 8, wherein the cytotoxic reagent is an entrapped fragment A of the diphtheria toxin.

10. The method of claim 8, wherein the antibody coating includes a long chain ($C_{12}$–$C_{24}$) fatty acid segment.

11. The method of claim 10, wherein the fatty acid segment is derived from palmitic acid.

12. The method of claim 8, wherein the antibody is a monoclonal antibody.

13. The method of claim 8, wherein the antibody recognizes a specific antigen on the surface of a target cell.

14. The method of claim 13, wherein the specific antigen recognized by the antibody is the major histocompatability antigen H-2K.

* * * * *